(12) United States Patent
McGahan et al.

(10) Patent No.: US 6,277,122 B1
(45) Date of Patent: Aug. 21, 2001

(54) DISTRACTION INSTRUMENT WITH FINS FOR MAINTAINING INSERTION LOCATION

(75) Inventors: Thomas V. McGahan, Memphis; Steven D. DeRidder, Bartlett, both of TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/418,741

(22) Filed: Oct. 15, 1999

(51) Int. Cl.⁷ .................................................. A61B 17/66
(52) U.S. Cl. ............................................ 606/90; 606/86
(58) Field of Search ........................ 606/53, 86, 90, 606/105; 600/570, 201, 210, 235

(56) References Cited

U.S. PATENT DOCUMENTS

| | | | |
|---|---|---|---|
| 2,437,329 | * 3/1948 | Moore | 600/570 |
| 2,514,665 | 7/1950 | Myller . | |
| 2,701,559 | * 2/1955 | Cooper | 600/569 |
| 2,854,981 | * 10/1958 | Morrison | 606/178 |
| 4,059,115 | 11/1977 | Jumashev et al. . | |
| 4,263,903 | * 4/1981 | Griggs | 606/75 |
| 4,545,374 | 10/1985 | Jacobson . | |
| 4,877,020 | * 10/1989 | Vich | 606/86 |
| 5,179,915 | * 1/1993 | Cohen et al. | 606/62 |
| 5,391,169 | * 2/1995 | McGuire | 606/79 |
| 5,484,437 | 1/1996 | Michelson . | |
| 5,630,819 | * 5/1997 | Ashby et al. | 606/81 |
| 5,700,264 | 12/1997 | Zucherman et al. . | |
| 5,720,751 | * 2/1998 | Jackson | 606/86 |
| 6,059,790 | * 5/2000 | Sand et al. | 606/99 |
| 6,086,595 | * 7/2000 | Yonemura et al. | 606/99 |

* cited by examiner

*Primary Examiner*—Gene Mancene
*Assistant Examiner*—Michael B. Priddy
(74) *Attorney, Agent, or Firm*—Woodard, Emhardt, Naughton, Moriarty & McNett (57) ABSTRACT

A tip for a medical device that distracts two opposing vertebral bodies. The tip has a hub, a boss, and a first longitudinal fin. The boss is attached the hub and has a body, a tapered portion, and a vertex. The first fin is attached to the boss, and projects from at least a portion of the boss's external surface. The first fin then extends over at least a portion of the length of the body and substantially extends over the length of the tapered portion.

22 Claims, 9 Drawing Sheets

DISTRACTION INSTRUMENT WITH FINS FOR MAINTAINING INSERTION LOCATION

The present invention relates to an apparatus for separating vertebral bodies to perform surgery or install implants in the disc space between vertebral bodies, and more specifically relates to an apparatus with one or more fins that extend from a substantial part of the tapered end and the body of the apparatus in order to maintain its insertion location between the vertebrae.

BACKGROUND

Distraction is a common surgical procedure to operate on the spine. It is used to prepare a spine for fusing two opposing (adjacent) vertebrae or to install an implant in the disc space between two opposing vertebrae. Distraction can be performed anteriorly (from the front of the patient) or posteriorly (from the back). But regardless of the approach, the procedure generally begins by first exposing that portion of the spine, which the surgeon has determined to require repair, and then removing all or part of the damaged spinal disc between the two opposing vertebrae in question.

After removing the spinal disc, the surgeon then typically inserts what the layperson may describe as one or more wedges between the two vertebrae. Each wedge is mounted on the end of a shaft and successively taller wedges are inserted between the two vertebrae until the surgeon obtains the desired separation ("distraction") between them. Once the desired separation is obtained, the surgeon then slides what the layperson may describe as a special tube over the shaft while the last wedge is still located between the vertebrae. This special tube is often referred to as a "guide sleeve". The guide sleeve is generally taller than the wedge that separates the vertebrae. Hence, the distal end (the end toward the patient) of the guide sleeve butts against the outside of the top and bottom vertebrae. Typically, the guide sleeve has a top spike and bottom spike that extend from its distal end, and these spikes are respectively placed in contact with the top and bottom vertebrae. Further, the end of the guide sleeve may have lateral extensions to extend into the disc space between the top and bottom vertebrae and around each side of the wedge. The spikes are then driven into the vertebrae by striking the proximal end of the outside sleeve distractor with a hammer or some other impact device. With the spikes placed into the vertebrae and the lateral extensions slid in the disc space, the wedge is no longer necessary to hold the vertebrae apart. The spikes and lateral extensions now serve that function, and the wedge can be pulled out from the disc space through the inside of the guide sleeve. With the wedge removed, the surgeon is then free to work through the inside of this special tube to prepare the disc space for fusion or install implants.

With the foregoing explanation in mind, some nomenclature is important to fully understand the following specification. If the wedge/tip used to separate the vertebrae is approximately as tall as it is wide, the operation is called a "single barrel" procedure. Alternatively, if the wedge/tip is approximately twice as wide as it is tall, the operation is called a "double barrel" procedure. This terminology has largely risen for metaphoric reasons. The cross-section of a guide sleeve used in a double-barrel procedure resembles the cross-section of a double-barrel shotgun, and the cross-section of the guide sleeve used in a single-barrel procedure resembles the cross-section of a single-barrel shotgun.

The insertion location of the wedges between the vertebrae is of critical importance in most any surgery involving vertebral distraction. The wedge/tip determines the placement of the guide sleeve, which in turn commonly determines the exact placement of an implant or fusion material within the disc space. Hence, prior art devices, such as that presented in U.S. Pat. No. 5,484,437 to Michelson seek to limit inadvertent migration of the wedge by incorporating sharp pegs into the top and bottom sides of the wedge. The pegs in that design, however, do not contact vertebral tissue until the distractor/wedge has all but fully separated the vertebrae in question. As a result, that prior art design may allow the distractor/wedge to migrate during insertion into the vertebral space, before the sharp pegs have the opportunity to function.

What is needed is a medical device that can immediately secure its position within the disc space between two vertebral bodies, once the surgeon places the device in contact with the spine. The following devices address this need.

SUMMARY OF THE INVENTION

In one aspect, this invention is a tip for a medical device that distracts two opposing vertebral bodies. The tip has (1) a hub, (2) a boss, and (3) a first longitudinal fin. The boss is attached to the hub and has a body, a tapered portion, and a vertex. The first longitudinal fin is attached to the boss, and projects from at least a portion of the boss's external surface. But in addition, the first longitudinal fin also extends over at least a portion of the length of the body and substantially extends over the length of the tapered portion of the boss.

In another aspect, this invention is a tip for a medical device that distracts two opposing vertebral bodies. The tip has (1) a hub, (2) a boss, (3) a first longitudinal fin, and (4) a second longitudinal fin. The boss is attached to the hub and has a body, a tapered portion, and a vertex. The first and second longitudinal fins are attached to the boss, and project from at least a portion of the boss's external surface. But in addition, the longitudinal fins also extend over at least a portion of the length of the body and substantially extend over the length of the tapered portion of the boss.

As used in this specification, the term "hub" is a part of this invention that holds the boss. The hub may have various shapes such as a wedge, a tube, a rectangle, a square, a parabola, or a dome.

As used in this specification, the term "boss" is a part of this invention that holds the longitudinal fins. The boss may have various shapes such as a wedge, a tube, a rectangle, a square, a parabola, or a dome.

As used in this specification, the term "substantially extending over the length of said tapered portion", which is used to describe the placement of a longitudinal fin on the present invention, means that the longitudinal fin distally extends over the tapered portion for no less than about 40 percent of the total length of the tapered portion, measured over the external surface of the tapered portion, between the tapered portion's proximal and distal ends.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, and that such alterations and further modifications in the illustrated device and that such further applications of the principles of the invention as illustrated therein are contemplated as would normally occur to one skilled in the art to which the invention pertains.

Figure 1:
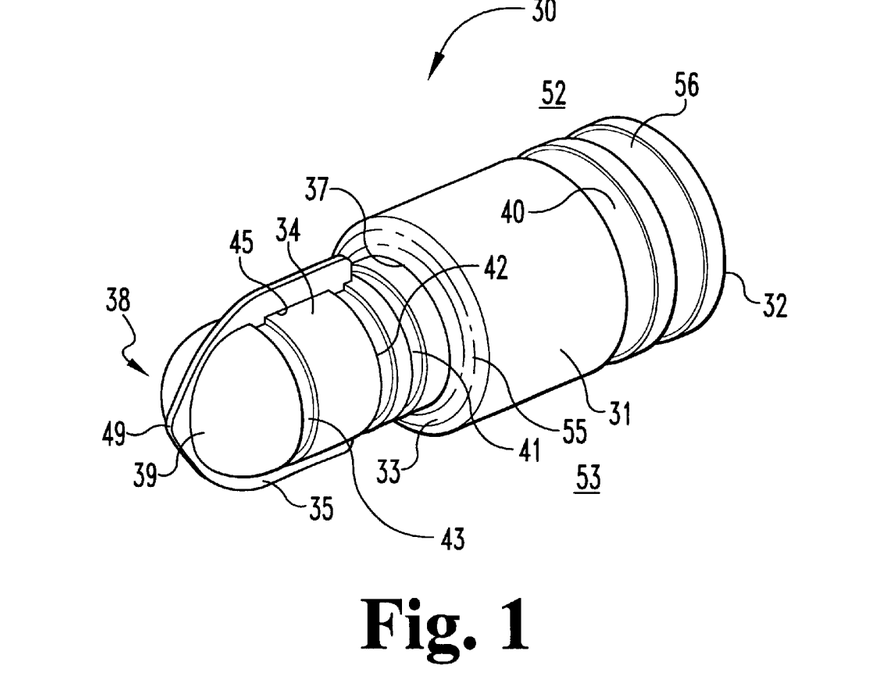
FIG. 1 is a perspective view of a tip for a medical device to distract two opposing vertebral bodies according to one embodiment of the present invention.
Figure 2:
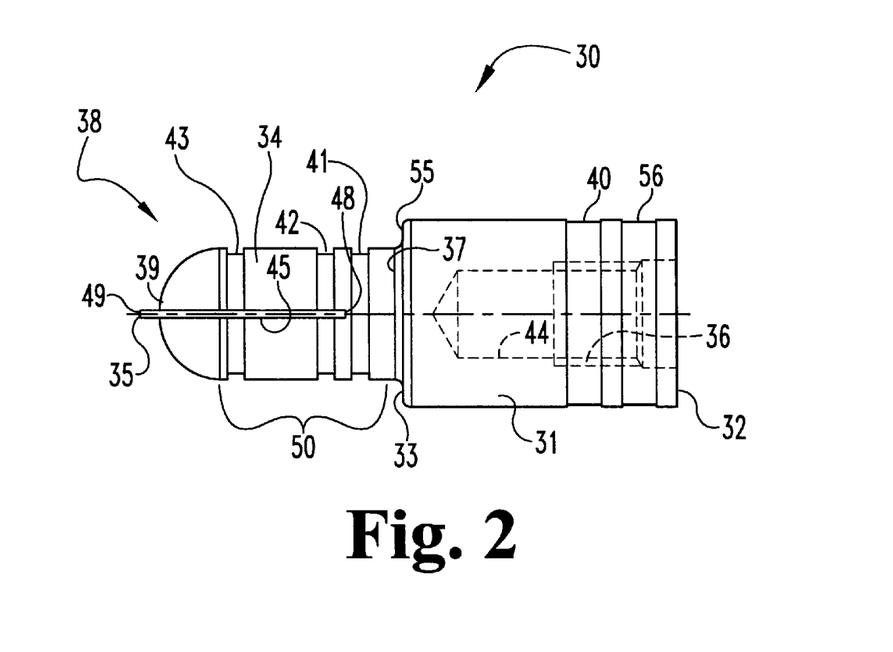
FIG. 2 is a plan view of a tip for a medical device to distract two opposing vertebral bodies according to one embodiment of the present invention.
Figure 3:
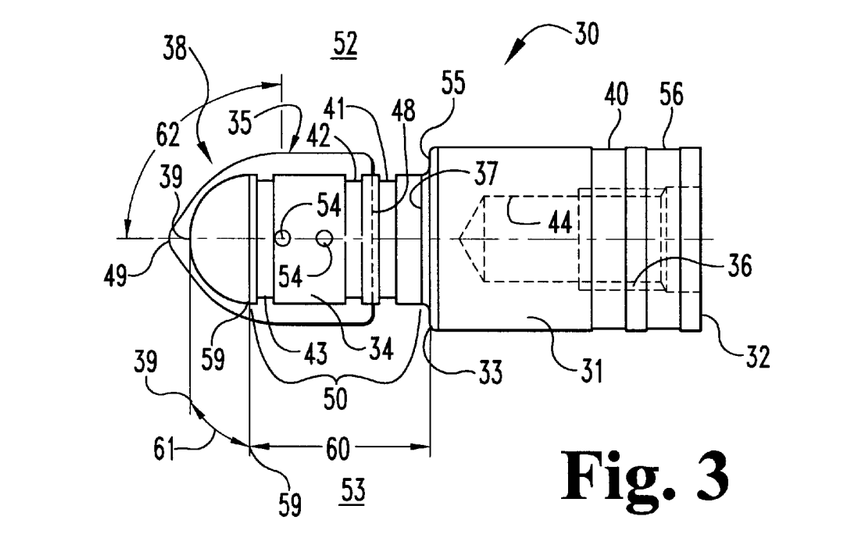
FIG. 3 is a side elevation view of a tip for a medical device to distract two opposing vertebral bodies according to one embodiment of the present invention.

Referring now to FIGS. 1–3, there is shown a tip 30 for a medical device that distracts two opposing vertebral bodies according to one embodiment of the present invention. Tip 30 includes a hub 31, a boss 34, and a longitudinal fin 35. Hub 31 has a proximal end 32, a distal end 33, and means for connecting proximal end 32 to the distal end of a medical device (not shown). In this embodiment, the means for connecting proximal end 32 to a medical device are female screw threads 36. As is common in the art, these threads are created by first drilling hole 44 into hub 31, followed by tapping threads 36 into the walls of hole 44. However besides female screw threads, other connecting means are contemplated to practice the present invention such as male screw threads, pinning, or welding. The end of hub 31 is also shown with bands 56 and 40. These bands are preferably colored to designate a tip of a particular size.

Boss 34 has a proximal end 37, a distal end 38, and a body 50 located between ends 37 and 38. Proximal end 37 is fixedly secured to the distal end 33 of hub 31 in any appropriate manner such as welding, however, both hub 31 and boss 34 are more preferably manufactured by directly machining hub 31 and boss 34 from a common piece of material. Nevertheless, hub 31 is also preferably larger than boss 34 so as to form shoulder 55 between hub 31 and boss 34. Body 50 has a length 60 (FIG. 3), and preferably, length 60 is such that tip 30 will not overly penetrate the disc space when shoulder 55 butts against the outside of the vertebrae. The distal end 38 of boss 34 is closed and preferably gets thinner at tapered portion 62 over a surface length 61 to a vertex 39. Similar to hub 31, boss 34 is cut with bands 41, 42, and 43; however, unlike the bands in the hub, these bands in boss 34 serve to engage tissue when the tip is in use. Finally, boss 34 is also cut with slot 45 to hold longitudinal fin 35, and preferably, slot 45 is cut completely through boss 34.

Now referring to FIGS. 1–4, longitudinal fin 35 has a proximal end 46 and a distal end 47 that preferably extends from boss 34 at vertex 39 and continues to extend from boss 34 for the entire surface length 61 of tapered portion 62. However, it is also contemplated that longitudinal fin 35 does not extend from surface length 61 for its entire dimension, that is from its distal end at vertex 39 to its proximal end 59. In this regard, it is also contemplated that longitudinal fin 35 may also be coterminous with the tapered portion (or simply does not extend from the surface of the tapered portion at this location) for up to about the 60 percent of surface length 61. And more preferably does not so extend for up to about the first, distal 60 percent of surface length 61. In other words, the fin 35 will extend from tapered portion 62 for about 40 percent or more of length 61 and leave a remaining 60 percent or less without a fin. But again, more preferably longitudinal fin 35 will extend from tapered portion 62 for about the first, proximal 40 percent or more of length 61 and leave a remaining distal 60 percent or less without a fin. An example of a 60 percent coterminous profile is depicted by the dashed line 64 in FIG. 4 with the dashed line representing the outside limits of boss 34 that reside next to fin 35. Dashed lines 65 and 66 respectively represent a fin with about a 20 percent and about a 10 percent coterminous profile.

Longitudinal fin 35 is preferably mechanically held in slot 45 by pins 54 (FIG. 3) or by a weld (not shown). The proximal end 46 of longitudinal fin 35 is preferably straight to ride against the bottom 48 of slot 45. The distal end 47, however, preferably terminates at a second vertex 49. Then as shown, longitudinal fin 35 preferably continues from vertex 49 to project laterally around the tapered portion 62 of distal end 38 and down at least a portion of body 50. Moreover, although longitudinal fin 35 is shown in FIG. 3 wrapping around both the top side 52 and the bottom side 53 of boss 34, it is also contemplated that longitudinal fin 35 may project only from one of these sides, not both. And still further, though fin 35 is shown as a separate piece, it is further contemplated that fin 35 and boss 34 are cast or machined from a common piece of material.

The tip shown in FIGS. 1–3 would typically be used in a single-barrel procedure and is further of a design that is capable of being removably attached to a medical device. In this regard, the reader should take note the present invention may take other forms. For example, this single barrel design could be permanently secured to a shaft as part of a larger medical device that is used to distract two opposing vertebrae, or this tip could be widened for use in a double-barrel procedure. For the convenience of the reader, an embodiment incorporating both of these options follows.

Figure 5:
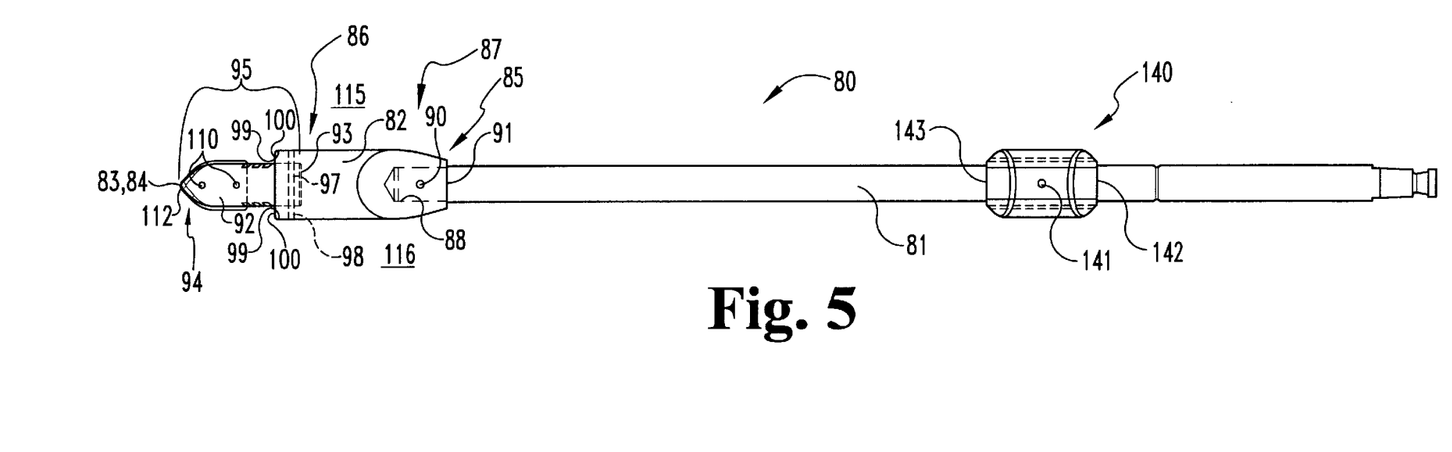
FIG. 5 is a side elevation view of a medical device to distract two opposing vertebral bodies according to another embodiment of the present invention.
Figure 6:
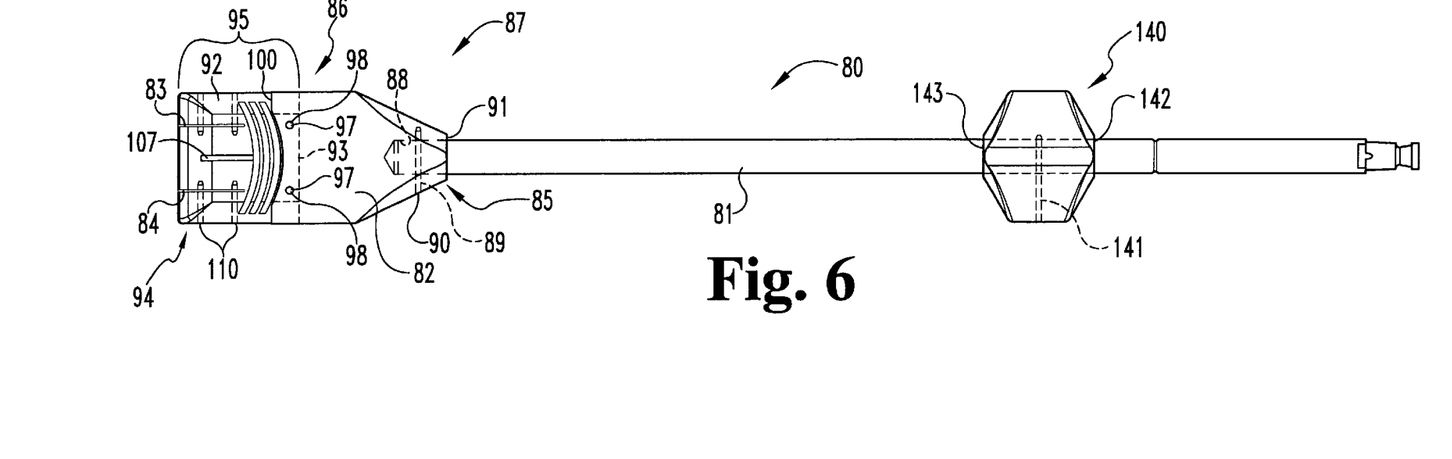
FIG. 6 is a plan view of a medical device to distract two opposing vertebral bodies according to another embodiment of the present invention.

Referring now to FIGS. 5 and 6, there is shown a medical device 80 that distracts two opposing vertebral bodies according to another embodiment of the present invention. Medical device 80 includes a shaft 81, a hub 82, a boss 92, a first longitudinal fin 83, and a second longitudinal fin 84. Hub 82 has a proximal end 85, a distal end 86, and means for connecting proximal end 85 of hub 82 to the distal end 87 of shaft 81. In this embodiment, the means for connecting proximal end 85 to shaft 81 is a pin and a weld. As is common in the art, such a joint is created by first drilling a hole 88 into hub 82 that is of slightly larger diameter than shaft 81. Shaft 81 is then inserted into hole 88, which is followed by drilling a much smaller hole 89 into the side of hub 82 and shaft 81 then inserting a pin 90 of appropriate diameter into hole 89. The circumference of shaft 81 is then welded to hole 88 at 91, and pin 90 is finished flush with the external surface of hub 82. However, besides pinning and welding, other connecting means are contemplated to practice the present invention such as mating male and female screw threads. Further details of Hub 82 using the same reference numerals as in FIGS. 5 and 6 are shown in FIGS. 16–20.

Figure 7:
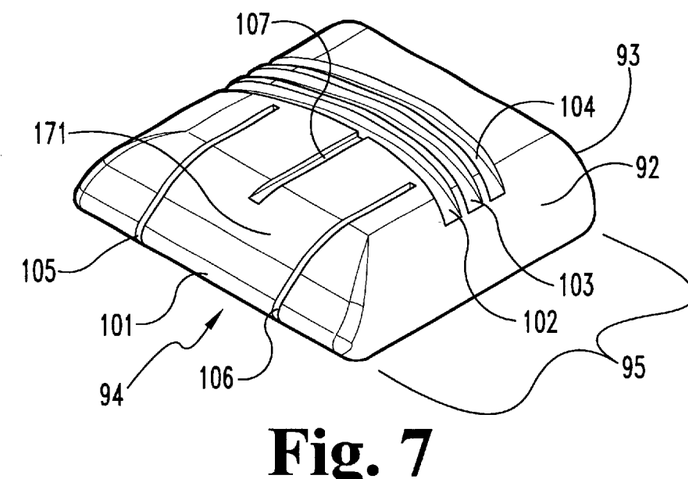
FIGS. 7–10 are respectively a perspective view, a plan view, an end view, and a cross-sectional view of a boss, which may be used to practice the present invention.
Figure 8:
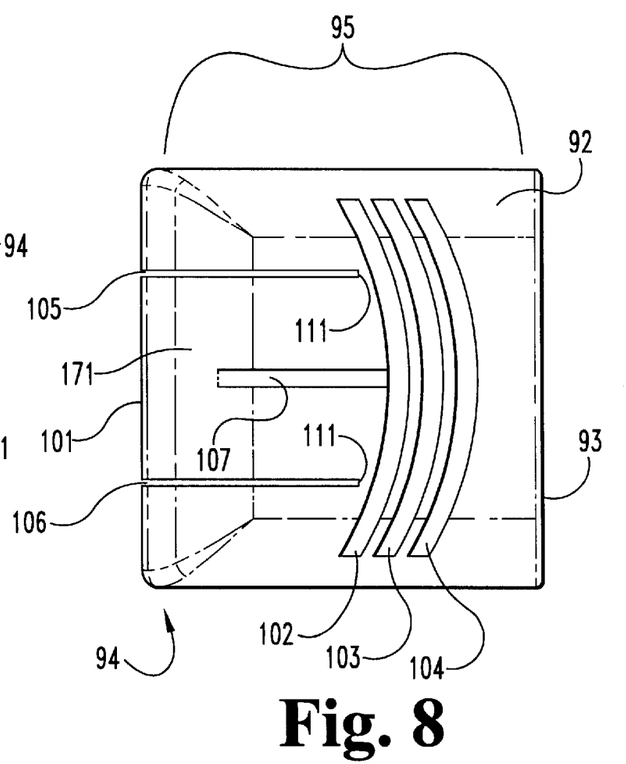
Figure 9:
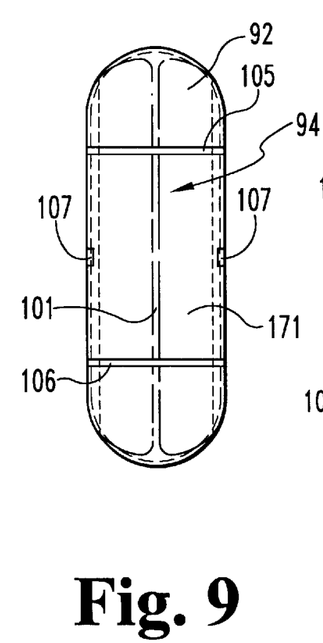
Figure 10:
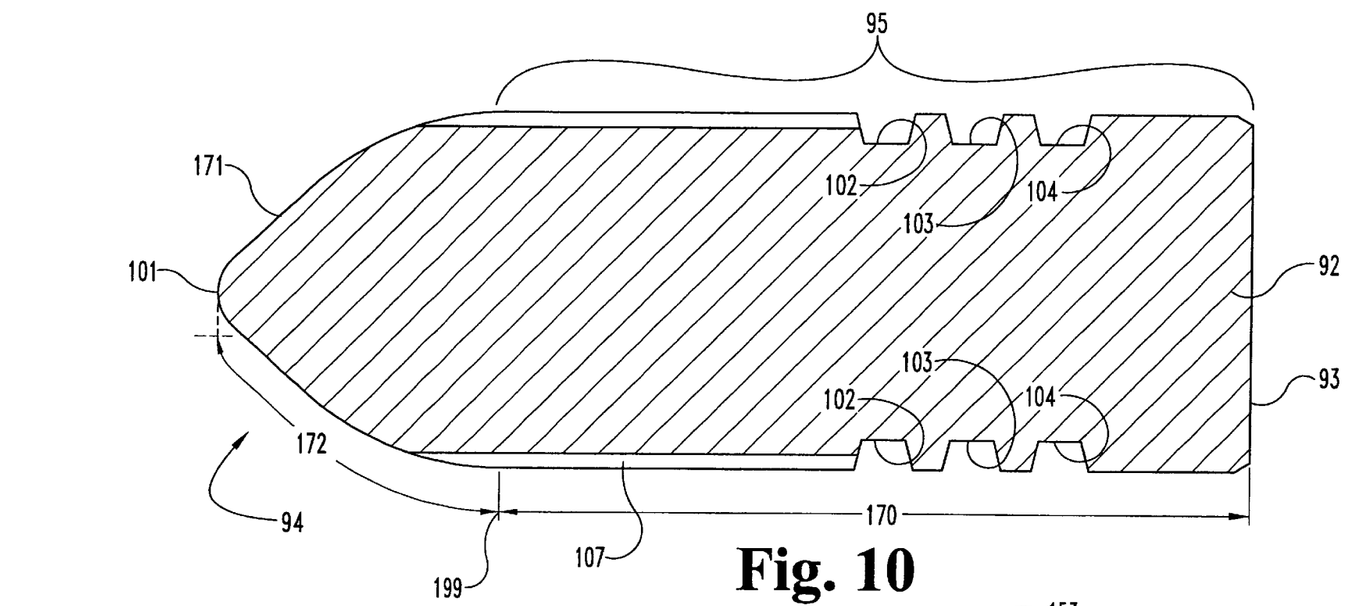
Figure 16:
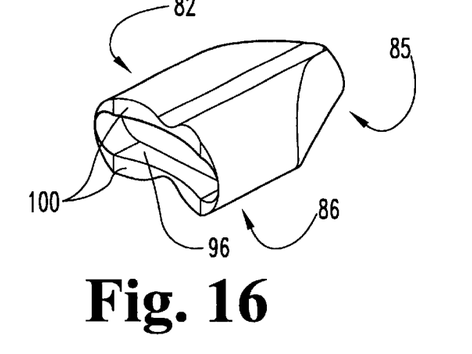
FIGS. 16 and 17 are respectively a front perspective view and a rear perspective of a hub, which may be used to practice the present invention.
Figure 17:
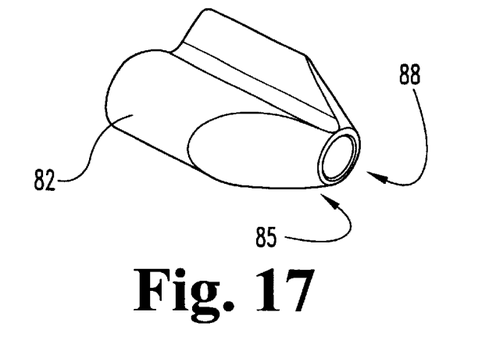
Figure 18:
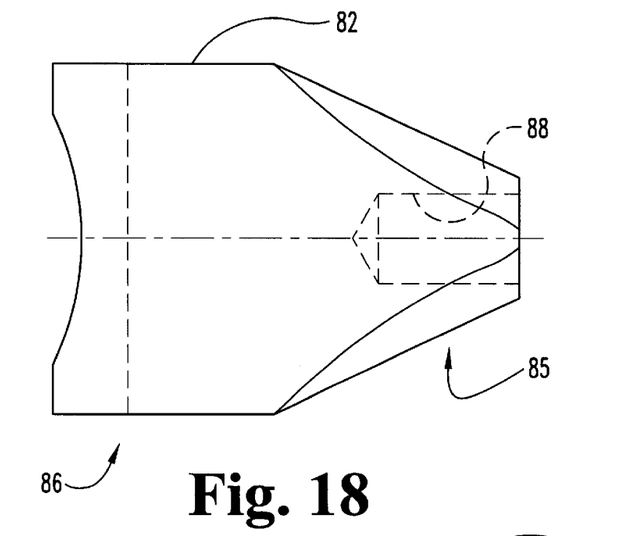
FIGS. 18–20 are respectively a plan view, side cross-section view, and an end view of a hub, which may be used to practice the present invention.
Figures 19, 20:
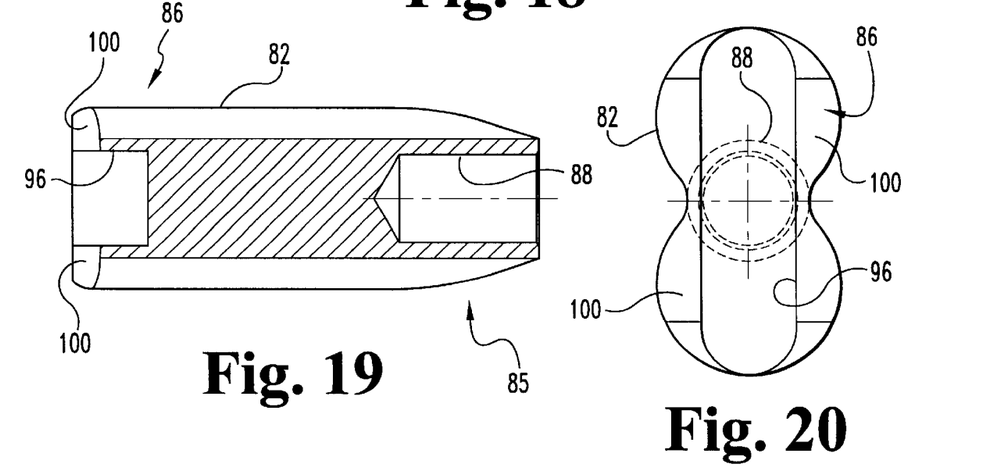

Referring now to FIGS. 5–10, boss 92 has a proximal end 93, a distal end 94, and a body 95 located between ends 93 and 94. Proximal end 93 is fixedly secured to the distal end 86 of hub 82 in any appropriate manner, such as being cast as a single piece, or machined from a single piece of material; however, boss 92 and hub 82 are preferably first pinned, then welded together. In this regard, proximal end 93 is placed in a mating slot 96 in hub 82 (FIGS. 16, 19, 20). Holes 97 (FIGS. 5, 6) are then drilled through hub 82 and boss 92, which is then followed by pinning (98) and welding the pins into place. Here again, as in the previously presented embodiment, hub 82 is preferably slightly larger than boss 92 so as to from shoulder 100 between hub 82 and boss 92. Body 95 has a length 170 (FIG. 10), and preferably length 170 is such that device 80 will not overly penetrate the disc space when shoulder 100 butts against the outside of the vertebrae. The distal end 94 of boss 92 is closed and preferably gets thinner at tapered portion 171 over a surface length 172 to a vertex 101. Similar to the grooves cut in the boss of the previous embodiment, boss 92 is cut, preferably on each side, with grooves 102, 103, and 104 (FIGS. 7 and 8), which serve to engage tissue when the medical device is in use. Finally boss 92 is also cut with slots 105 and 106, and channels 107 (FIGS. 7–9). Slots 105 and 106 are preferably cut completely through boss 92. These slots are used to hold a first longitudinal fin 83 and a second longitudinal fin 84. Channels 107 serve to inform the user where the midline of medical device 80 is located when the device is in use and placed between two vertebrae.

Figure 4:
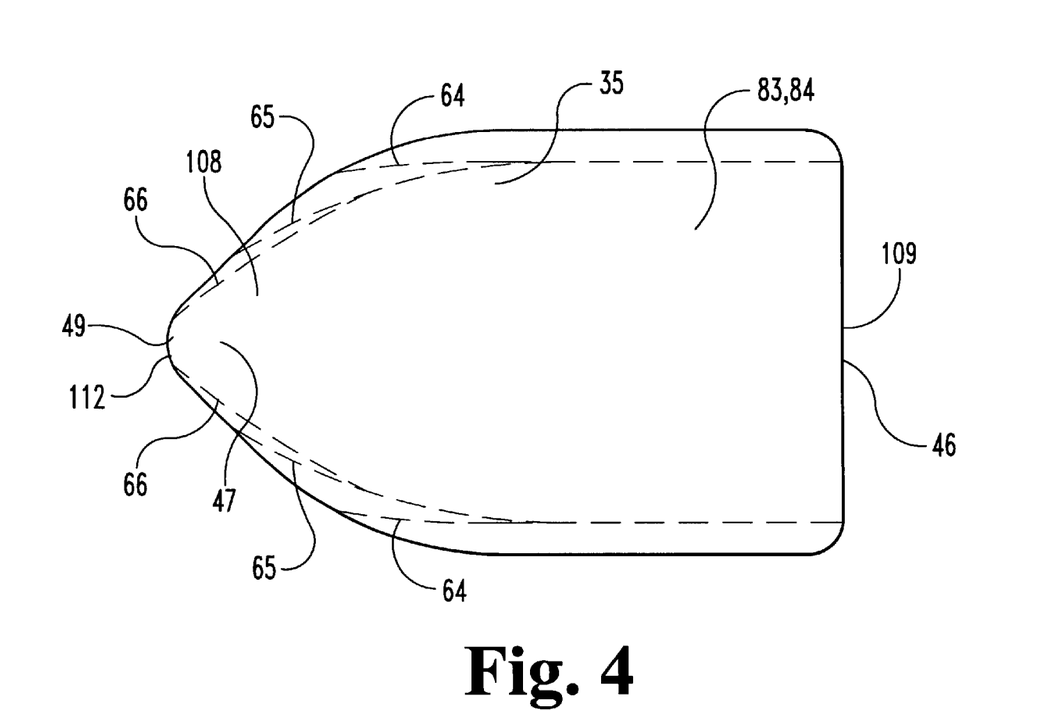
FIG. 4 is a side elevation view of a longitudinal fin, which may be used to practice the present invention.

Now referring to FIGS. 4–6, longitudinal fins 83 and 84 are preferably identical to previously presented longitudinal fin 35, however, for the convenience of the reader, this information will be presented again using different reference numerals for this embodiment of the present invention. Longitudinal fins 83 and 84 have a distal end 108 and a proximal end 109 that preferably extends from boss 92 at vertex 101 and continues to extend from boss 92 for the entire surface length 172 of tapered portion 171. However, it is also contemplated that longitudinal fins 83 and 84 do not extend from surface length 171 for its entire dimension. That is from tapered portion's distal end at vertex 101 to its proximal end 199 (or simply does not extend from the surface of the tapered portion at this location) for up to about 60 percent of surface length 172. And preferably does not extend for up to about the first, distal 60 percent of surface length 172. In other words, longitudinal fins 83 and 84 will extend from tapered portion 171 for about 40 percent or more of length 172 and leave a remaining 60 percent or less without a fin. But again, preferably longitudinal fins 83 and 84 will extend from tapered portion 171 for about the first, proximal 40 percent or more of length 172 and leave a remaining distal 60 percent or less without a fin. Examples of 60 percent, 20 percent, and 10 percent coterminous profiles are shown in previously presented FIG. 4 at dashed lines 64, 65, and 66.

Longitudinal fins 83 and 84 are preferably mechanically held in slots 105 and 106 by pins 110 or a weld (not shown). The proximal ends 109 of longitudinal fins 83 and 84 are preferably straight to ride against the bottom 111 (FIG. 8) of slots 105 and 106. The distal end 108, however, preferably terminates at a second vertex 112. Longitudinal fins 83 and 84 each then preferably continue from vertex 112 to project laterally around distal end 94 of boss 92 and down at least a portion of body 95. Moreover, although longitudinal fins 83 and 84 are shown in FIG. 5 wrapping around both the top side 115 and the bottom side 116 of boss 92, it is also contemplated that longitudinal fins 83 and 84 each project only from one of these sides, not both.

Referring now to FIGS. 5, 6, and 13–15, medical device 80 preferably also includes aft guide 140 fixedly secured to shaft 81. Both aft guide 140 and hub 82 preferably have a cross-section to slide within an outer distractor sleeve. And here, the distractor would be one typically used in a double-barrel procedure because, referring to FIG. 15, the cross-section of aft guide 140 is approximately twice as wide as it is tall and resembles a figure "8". In this embodiment, aft guide 140 is first drilled at 144 to a diameter that is slightly larger than shaft 81. Thereafter, aft guide 140 is slid over shaft 81 and located over the length of shaft 81 at a desired location in line with hub 82 and boss 92. Aft guide 140 is then first pinned at 141 and then welded at 142 and 143 to secure it to shaft 81. Beyond pinning and welding, other methods to attach aft guide 140 to shaft 81 are contemplated by this invention, for example, by casting aft guide 140 and shaft 81 from a common piece of material.

Figure 11:
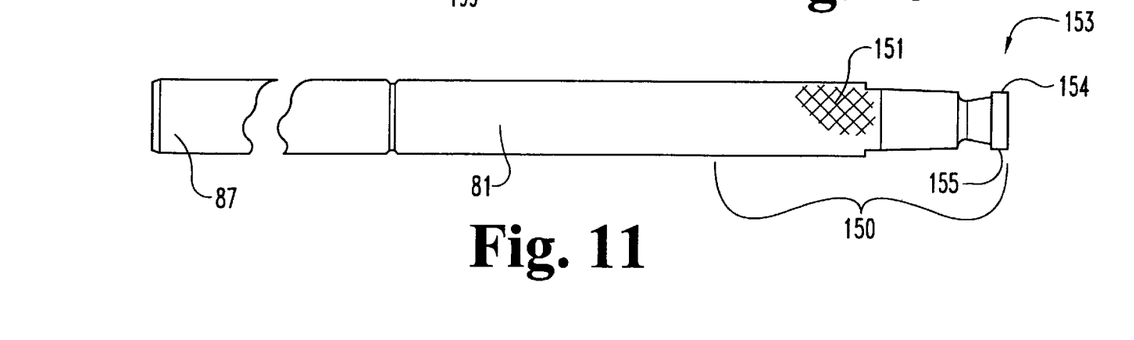
FIGS. 11–12 are respectively a side elevation view and an end view of a shaft, which may used to practice the present invention.
Figure 12:
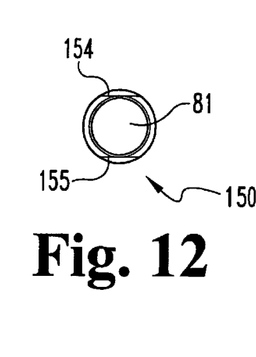
Figure 13:
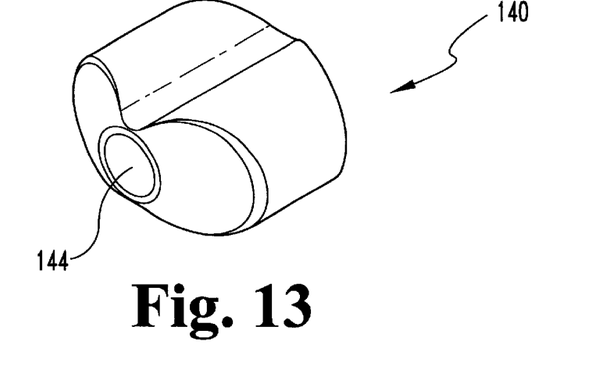
FIGS. 13–15 are respectively a perspective view, a plan view, and an end view of an aft guide, which may be used to practice the present invention.
Figure 14:
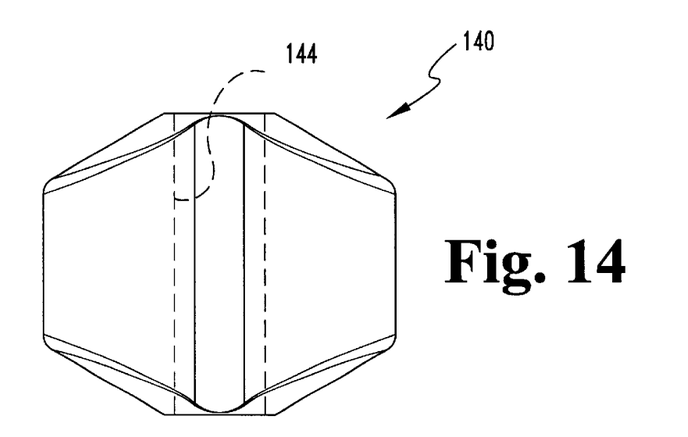
Figure 15:
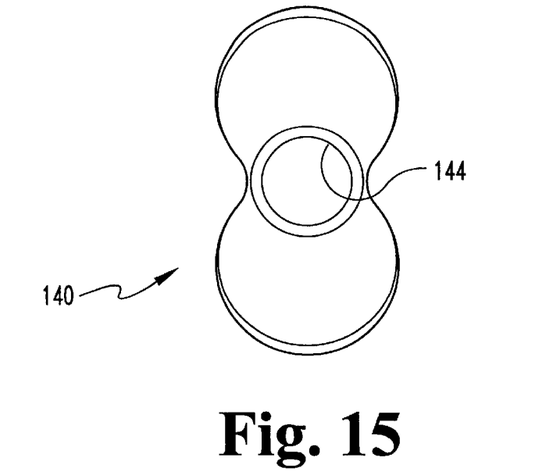

Additional details of shaft 81 are further shown in FIGS. 11 and 12. The area 150, which is proximal to aft guide 140, is preferably knurled at 151 to assist the user in gripping the device. Moreover, the proximal end 152 of shaft 81 is further adapted at 153 to accept a removable handle (not shown). In this embodiment, the adaptation 153 comprises a male fitting with two flat sides 154 and 155. A complementary female fitting, which is attached to a handle, then engages shaft 81 by sliding over the male fitting. The handle can then control rotation of the shaft because the mating female fitting has complementary flat sides (not shown) that ride against mating flat sides 104, 105 on end of shaft 81.

Figure 21:
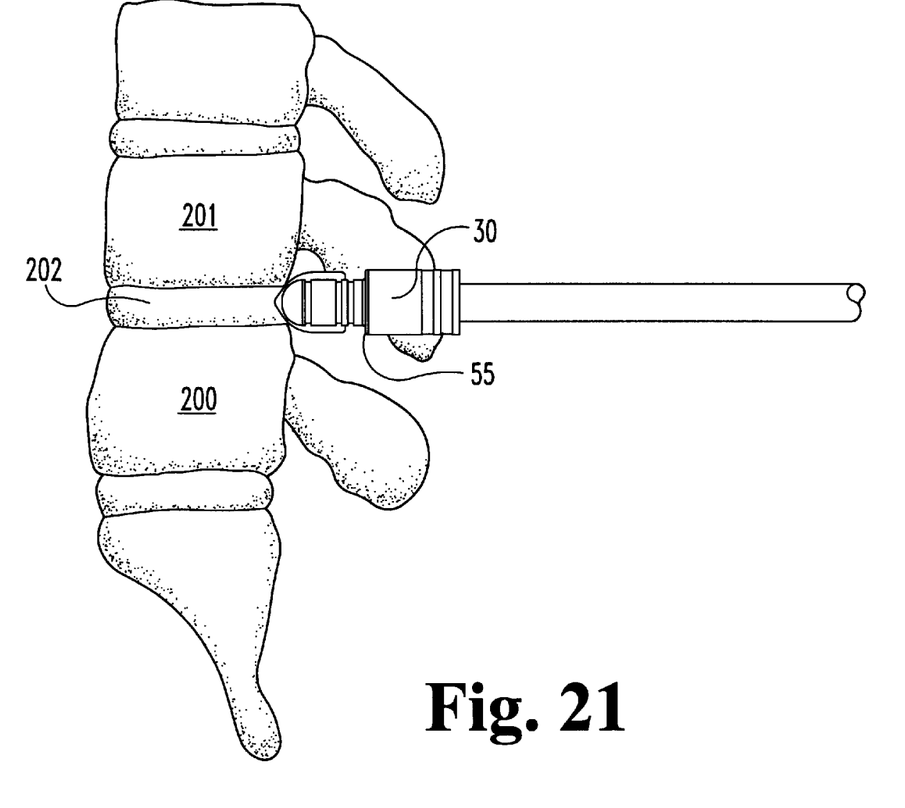
FIG. 21 is a side elevation view of one embodiment of the present invention being inserted between two opposing vertebral bodies.

Each of the foregoing embodiments of the present invention is generally used in the same manner. With the spinal disc removed, the surgeon places the leading edge of the longitudinal fins on the distal end of the distractor device into the disc space and against the surrounding vertebrae 200, 201. (FIG. 21) Once properly located, the surgeon then drives the distal end of the distractor device between the vertebrae and into the disc space 202. Upon entry, the longitudinal fins immediately cut into the surrounding vertebrae, which helps prevent the distractor device from deviating from the desired line of entry. A surgeon typically drives the device into the disc space until shoulder 55 or 100 comes to rest against the outside of vertebrae 200, 201. Once fully inserted, the surgeon typically either removes the device and reinserts a taller device to further separate the vertebrae, or if the desired separation has been reached, the surgeon installs a guide sleeve. With the guide sleeve in place, the surgeon then removes the device from between the vertebrae and continues the rest of the operation through the guide sleeve.

Figure 22:
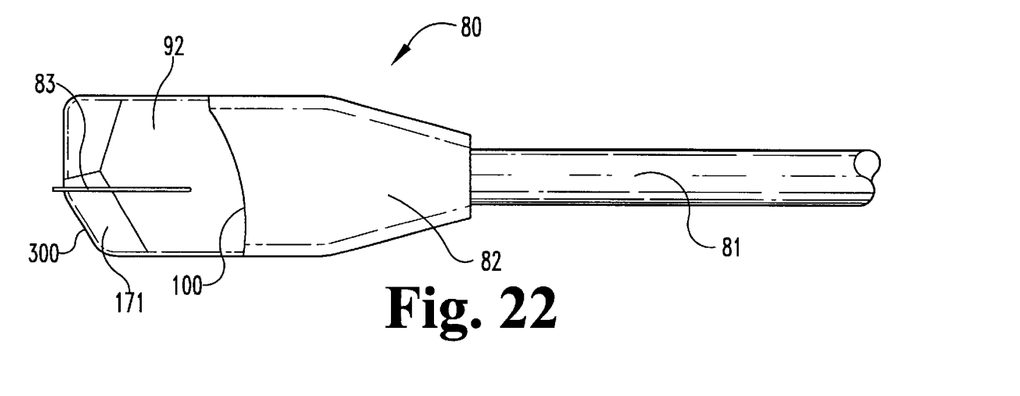
FIGS. 22–24 are respectively a top, side, and bottom view of yet another embodiment of the present invention.
Figure 23:
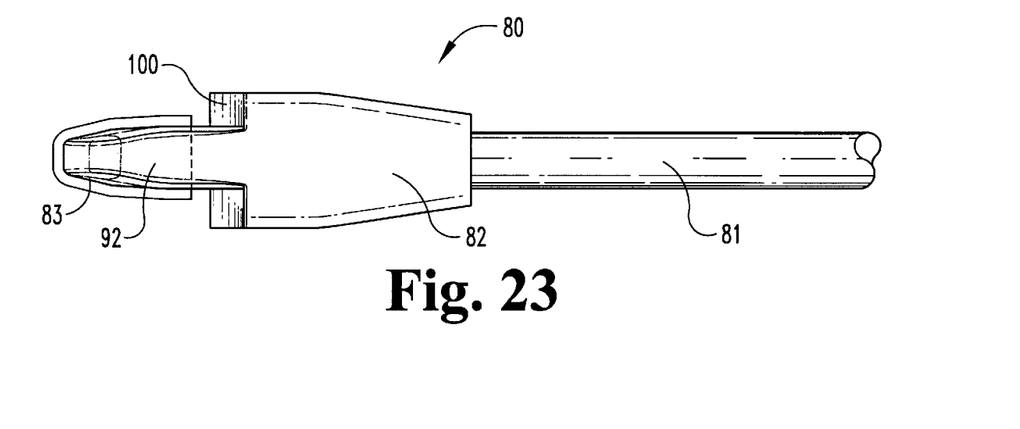
Figure 24:
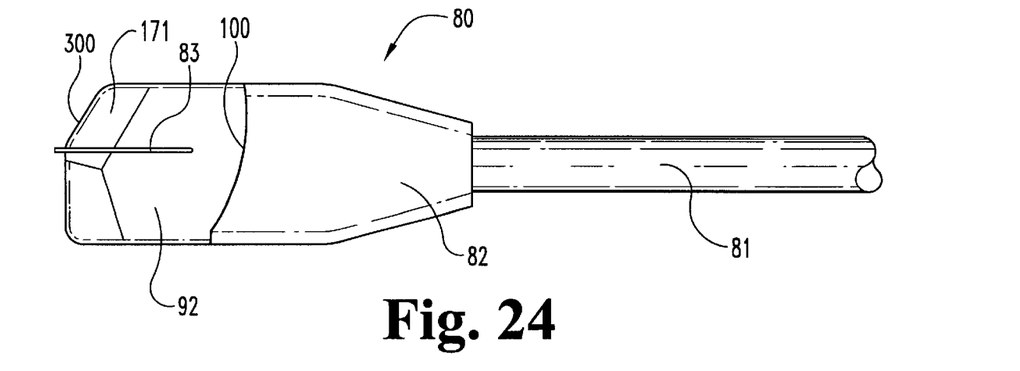

Referring now to FIGS. 22–24, there is shown yet another embodiment of the present invention. For the convenience of the reader, like numerals have been used to identify similar parts of this invention as that used in the embodiment shown in FIGS. 5–10. The embodiment shown in FIGS. 22–24, however, is for use when the surgeon must approach the spine from an angle. Here, medical distractor 80 has an oblique edge 300, which is typically required for the surgeon to distract adjacent vertebral bodies from a non-perpendicular angle. Relevant here, oblique angle 300 emphasizes the importance of the present invention. Longitudinal fin 83 helps insure that medical distractor 80 will maintain the proper line of insertion, even though oblique angle 300 may tend to force distractor 80 to move laterally. Immediately upon contact with the vertebral bodies, longitudinal fin 83 cuts into the vertebrae to help maintain the proper line of insertion into the disc space even before oblique angle 300 has the opportunity to cause a lateral misalignment.

An advantage of this invention over the prior art largely rests in the unique placement of the longitudinal fins 35 or 83–84 over a substantial part of the tapered portion of the boss that supports the longitudinal fin. Unlike the devices found in the prior art, the present invention places one or more guiding longitudinal fins in contact with vertebral bodies before they are fully distracted. This placement allows the longitudinal fins to help maintain the surgeon's line of insertion before the distractor device starts to separate the opposing vertebrae. And this assistance is far from minor. As explained earlier, the location of these "wedges" within the disc space can ultimately determine the exact placement of spinal implants or fusion material. Hence, maintaining the proper line of insertion of a distractor device at the start is important to help assure that the surgery will ultimately be a success.

What is claimed is:

1. A tip for a medical device to distract two opposing vertebral bodies, said tip comprising:
    (a) a hub with proximal and distal ends;
    (b) a boss, said boss fixedly secured to the distal end of said hub, said boss having a body, said body having a length; said boss further having an external surface, and a tapered portion distal to said body, said tapered portion having a length; and said boss further having a first vertex distal to said tapered portion; and
    (c) a first longitudinal fin, said first longitudinal fin fixedly secured to said boss, said first longitudinal fin projecting from at least a portion of the external surface of said boss, said first longitudinal fin extending over at least a portion of the length of said body and substantially extending over the length of said tapered portion;
    wherein the tip is adapted to be positioned between the two opposing veterbral bodies;
    wherein the tip is adapted to distract the two opposing vertebral bodies; and
    wherein said first longitudinal fin is adapted to maintain the position of the tip between the two opposing vertebral bodies.

2. The tip of claim 1, where said first longitudinal fin is coterminous with said first vertex.

3. The tip of claim 1, where said first longitudinal fin projects distally of said first vertex.

4. The tip of claim 1, including means for connecting the proximal end of said hub to the distal end of a medical device.

5. The tip of claim 1, where said first longitudinal fin laterally projects out from at least a portion of the body of said boss on two opposing sides of said boss.

6. The tip of claim 1, where said first longitudinal fin perpendicularly projects from the external surface of said boss.

7. The tip of claim 1, where said first longitudinal fin includes a second vertex projecting distally of said first vertex of said boss.

8. A tip for a medical device to distract two opposing vertebral bodies, said tip comprising:
    a hub with proximal and distal ends;
    a boss, said boss fixedly secured to the distal end of said hub, said boss having a body, said body having a length; said boss further having an external surface, and a tapered portion distal to said body, said tapered portion having a length; and said boss further having a first vertex distal to said tapered portion; and
    a first longitudinal fin, said first longitudinal fin fixedly secured to said boss, said first longitudinal fin projecting from at least a portion of the external surface of said boss, said first longitudinal fin extending over at least a portion of the length of said body and substantially extending over the length of said tapered portion;
    where said hub extends laterally beyond said boss thereby forming a shoulder between said hub and said boss.

9. A tip for a medical device to distract two opposing vertebral bodies, said tip comprising:
    a hub with proximal and distal ends;
    a boss, said boss fixedly secured to the distal end of said hub, said boss having a body, said body having a length; said boss further having an external surface, and a tapered portion distal to said body, said tapered portion having a length; and said boss further having a first vertex distal to said tapered portion;
    a first longitudinal fin, said first longitudinal fin fixedly secured to said boss, said first longitudinal fin projecting from at least a portion of the external surface of said boss, said first longitudinal fin extending over at least a portion of the length of said body and substantially extending over the length of said tapered portion; and
    a second longitudinal fin fixedly secured to said boss, said second longitudinal fin projecting from at least a portion of the external surface of said boss, said second longitudinal fin extending over at least a portion of the length of said body and substantially extending over the length of said tapered portion, and said second longitudinal fin being located substantially parallel to said first longitudinal fin.

10. The tip of claim 9, where said first and second longitudinal fins are coterminous with said first vertex.

11. The tip of claim 9, where said first and second longitudinal fins project distally of said first vertex of said boss.

12. The tip of claim 9, where said first and second longitudinal fins laterally project down at least a portion of the body of said boss on two opposing sides of said boss.

13. A medical device for distracting two opposing vertebral bodies, said medical device comprising:
    (a) a shaft, said shaft having a distal end;
    (b) a hub with proximal and distal ends, the proximal end of said hub being fixedly secured to the distal end of said shaft;
    (c) a boss, said boss fixedly secured to the distal end of said hub, said boss having a body, said body having a length; said boss further having an external surface, and a tapered portion distal to said body, said tapered portion having a length; and said boss further having a first vertex distal to said tapered portion; and (d) a first longitudinal fin, said first longitudinal fin fixedly secured to said boss, said first longitudinal fin projecting from at least a portion of the external surface of said boss, said first longitudinal fin extending over at least a portion of the length of said body and substantially extending over length of said tapered portion;

wherein the fin is sized to distract the two opposing vertebral bodies; and wherein the fin is adapted to cut into the two opposing vertebral bodies.

14. The medical device of claim 13, where said first longitudinal fin is coterminous with said first vertex.

15. The medical device of claim 13, where said first longitudinal fin projects distally of said first vertex.

16. The medical device of claim 13, where said first longitudinal fin laterally projects out from at least a portion of the body of said boss on two opposing sides of said boss.

17. The medical device of claim 13, where said first longitudinal fin perpendicularly projects from the external surface of said boss.

18. The medical device of claim 13, where said first longitudinal fin includes a second vertex projecting distally of said first vertex of said boss.

19. A medical device for distracting two opposing vertebral bodies, said medical device comprising:

a shaft, said shaft having a distal end;

a hub with proximal and distal ends, the proximal end of said hub being fixedly secured to the distal end of said shaft;

a boss, said boss fixedly secured to the distal end of said hub, said boss having a body, said body having a length; said boss further having an external surface, and a tapered portion distal to said body, said tapered portion having a length; and said boss further having a first vertex distal to said tapered portion; and a first longitudinal fin, said first longitudinal fin fixedly secured to said boss, said first longitudinal fin projecting from at least a portion of the external surface of said boss, said first longitudinal fin extending over at least a portion of the length of said body and substantially extending over the length of said tapered portion;

where said hub extends laterally beyond said boss thereby forming a shoulder between said hub and said boss.

20. A medical device for distracting two opposing vertebral bodies, said medical device comprising:

a shaft, said shaft having a distal end;

a hub with proximal and distal ends, the proximal end of said hub being fixedly secured to the distal end of said shaft;

a boss, said boss fixedly secured to the distal end of said hub, said boss having a body, said body having a length; said boss further having an external surface, and a tapered portion distal to said body, said tapered portion having a length; and said boss further having a first vertex distal to said tapered portion;

a first longitudinal fin, said first longitudinal fin fixedly secured to said boss, said first longitudinal fin projecting from at least a portion of the external surface of said boss, said first longitudinal fin extending over at least a portion of the length of said body and substantially extending over the length of said tapered portion; and a second longitudinal fin fixedly secured to said boss, said second longitudinal fin projecting from at least a portion of the external surface of said boss, said second longitudinal fin extending over at least a portion of the length of said body and substantially extending over the length of said tapered portion, and said second longitudinal fin being located substantially parallel to said first longitudinal fin.

21. The medical device of claim 20, where said first and second longitudinal fins are coterminous with said first vertex.

22. The medical device of claim 20, where said first and second longitudinal fins project distally of said first vertex of said boss.

* * * * *

UNITED STATES PATENT AND TRADEMARK OFFICE
CERTIFICATE OF CORRECTION

PATENT NO.    : 6,277,122 B1
DATED         : August 21, 2001
INVENTOR(S)   : Thomas V. McGahan et al.

It is certified that error appears in the above-identified patent and that said Letters Patent is hereby corrected as shown below:

<u>Title page</u>,
Item [75], after "Memphis;" please change "Steven D. DeRidder" to -- Stephen D. De Ridder --.

Signed and Sealed this

Eleventh Day of June, 2002

Attest:

Attesting Officer

JAMES E. ROGAN
*Director of the United States Patent and Trademark Office*